US00PP10152P

United States Patent [19]

Sousa

[11] Patent Number: Plant 10,152

[45] Date of Patent: Dec. 16, 1997

[54] HYDRANGEA PLANT NAMED 'RAVEL'

[75] Inventor: Jose R. Sousa, Half Moon Bay, Calif.

[73] Assignee: Bay City Flower Company, Half Moon Bay, Calif.

[21] Appl. No.: 675,780

[22] Filed: Jul. 5, 1996

[51] Int. Cl.[6] ..... A01H 5/00

[52] U.S. Cl. ..... Plt./67.1

[58] Field of Search ..... Plt./67.1

[56] References Cited

U.S. PATENT DOCUMENTS

P.P. 9,510 4/1996 Ebihara ..... Plt./67.1

*Primary Examiner*—Howard J. Locker
*Assistant Examiner*—Kent L. Bell
*Attorney, Agent, or Firm*—James R. Cypher

[57] ABSTRACT

This invention relates to a new and distinct cultivar of *Hydrangea macrophylla* (Thunb.) named 'Ravel' which originated as a sport from the inventor's controlled commercial growing of the non-patented *Hydrangea macrophylla* cultivar 'Merritts Supreme', and is distinguished from its parent by the unique pigmentation pattern which causes the florets and inflorescence to be both pink and white, and gives each floret a white center and four pink fan-shaped points at the outer edges, resulting in a pink and white flower at the peak of its bloom, not predominantly a pink flower. The new variety 'Ravel' further possesses the favorable characteristics of: agressive, compact growth habit; long lasting large flowers and the ability to be easily forced in a greenhouse for flowering in the spring.

3 Drawing Sheets

BACKGROUND OF THE INVENTION

This invention relates to a new and distinct cultivar of the Saxifragaceae family. The botanical name of the plant is *Hydrangea macrophylla* (Thunb.). The varietal denomination is 'Ravel'. The new cultivar originated as a sport discovered five years ago growing among a commercial production of the common Hydrangea variety 'Merritts Supreme' in a controlled environment. 'Ravel' is distinguished from its parent and all other varieties of Hydrangea, of which I am aware, by the distinctive pigmentation pattern in its sepals which causes the florets and inflorescence to be both pink and white, and results in the appearance of the plant as having a pink and white flower. The naturally occuring colors of Hydrangea plants are either uniformly pink, uniformly blue or solid white depending on the pH and nutrients of the soil, and these are the plants most commonly available and grown. Hydrangea plants having mixed white and pink or white and blue flower coloring are new and not in common use. This new cultivar has been successfully asexually reproduced under controlled environmental conditions at a nursery in Half Moon Bay, Calif. under the direction of the inventor over a five year period with its distinguishing characteristics remaining stable.

Sepal color of 'Ravel' is white with blue or pink pigmentation. Blue or pink sepal pigmentation of individual *Hydrangea macrophylla* plants depends on the nutrients and pH of the growing medium. The unique pigmentation pattern which gives the new cultivar a pink and white or blue and white flower is created by the sepals being white at the base and colored at the tips. The outermost points, or tips, of the sepals are darkest in color, gradually spreading and shading to a lighter color and disappearing into the white base of the sepal. This gives each floret the appearance of being white with four pink or blue fan-shaped points at the outer edges. The pigmentation starts with a small amount of color appearing on the outermost tip of each sepal, and the color gradually spreads out to the sides and down the center as the flower grows and blooms. The color becomes diluted as it spreads sideways at the tip and down the center, finally fading away leaving the white color at the base of the sepal;

resulting in the fan-shaped appearance of the pigmentation. When the plant is at its peak bloom, it appears to be uniformly pink and white. This fan-shaped appearance of the pigmentation can be seen even in very old blooms that develop chlorophyll as they fade and die. The sepal coloration of the parent, 'Merritts Supreme', is uniformly pink or blue. While there are other Hydrangeas with a coloration pattern on their sepals, none of the other known varieties of Hydrangeas have the particular pattern of 'Ravel'. The new variety of Hydrangea as described herein is further distinguished from 'Merrits Supreme' by its more aggressive growth habit, and its larger flowers. Mature flowers slowly fade to green and ultimately brown with age. Both the new cultivar and 'Merritts Supreme' have long lasting flowers with tight full heads and can easily be forced in a greenhouse.

Asexual reproduction was first accomplished when vegetative cuttings were taken by the inventor from the initially discovered plant. Examination of asexually reproduced, successive generations, grown in a controlled environment at Half Moon Bay, Calif., show that the combination of characteristics as herein disclosed for 'Ravel' is firmly fixed. Asexual reproduction of successive generations at Half Moon Bay was achieved by taking vegetative cuttings from selected plants, over a period of five years. Each new generation over the five years retained the combination of characteristics as herein disclosed for 'Ravel'.

DESCRIPTION OF THE DRAWINGS

The accompanying drawings consist of color photographs that show the typical plant form, including the inflorescence, foliage, and unique sepal pigmentation pattern. 'Ravel' is shown with a pink and white sepal pigmentation pattern, but a blue and white pigmentation pattern is also possible by manipulation of the nutrient amendments and the pH of the growing medium. The colors are represented as truly as possible using conventional photographic procedures. The plants photographed are third generation plants.

DESCRIPTION OF THE NEW PLANT

Figure 1:
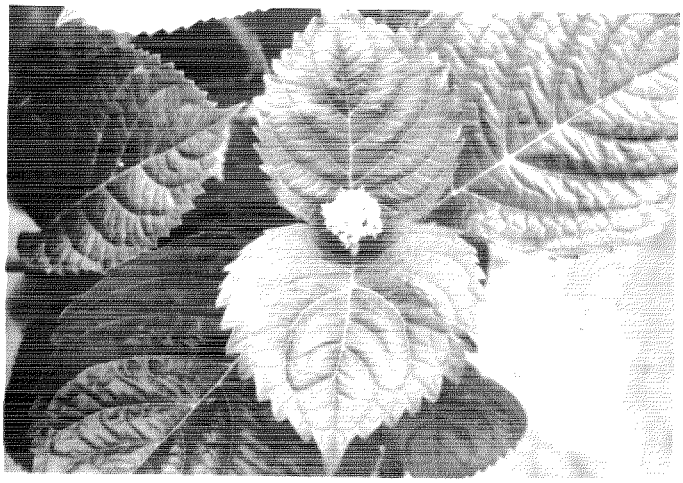
FIG. 1 is a view of a bud of the new cultivar.
Figure 2:
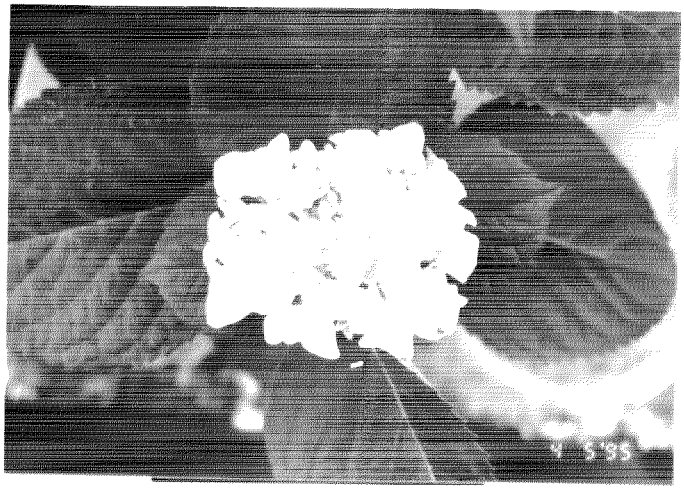
FIG. 2 is a close up view of the inflorescence showing the beginning of the appearance of color in the tips of the sepals as they grow and open up.
Figure 3:
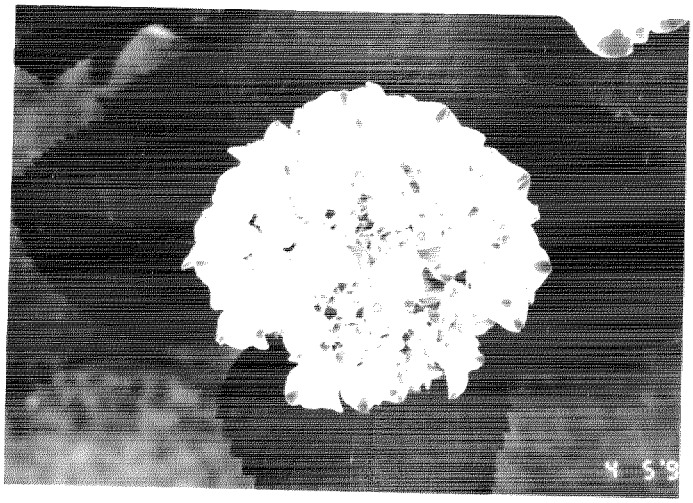
FIG. 3 is a close up view of the inflorescence showing the continuation of the growth of the sepals and the appearance of the pigmentation.
Figure 4:
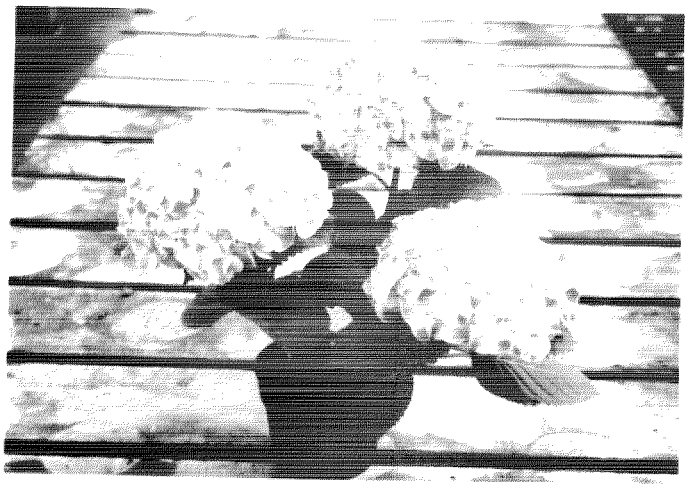
FIG. 4 is a view of the entire plant showing its form, growth habit, dark green foliage, inflorescence, and unique sepal pigmentation pattern at the peak of its blooming period.
Figure 5:
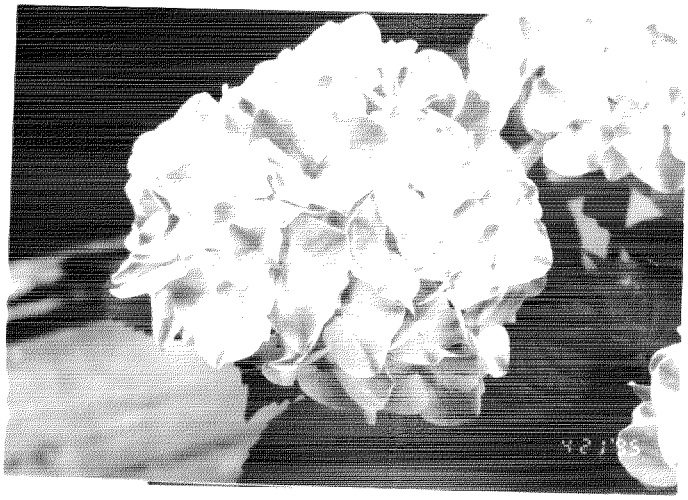
FIG. 5 is a close up view of one inflorescence at the peak of its blooming period.
Figure 6:
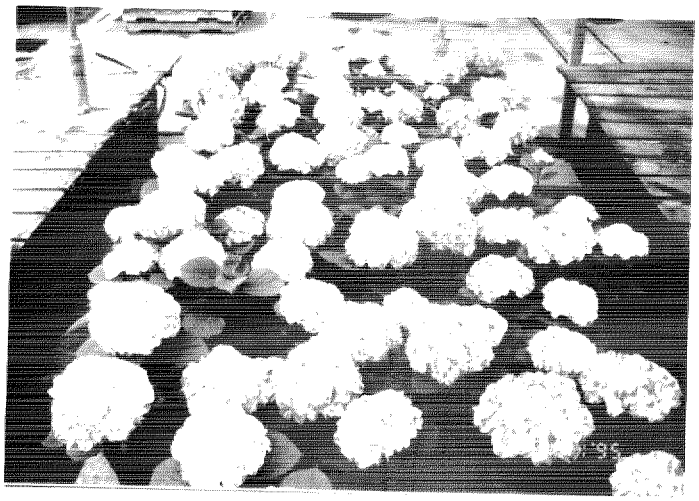
FIG. 6 is a view of multiple plants grouped together illustrating the pink and white flower at the peak of its bloom; not predominately a white flower or predominately a pink flower.
Figure 7:
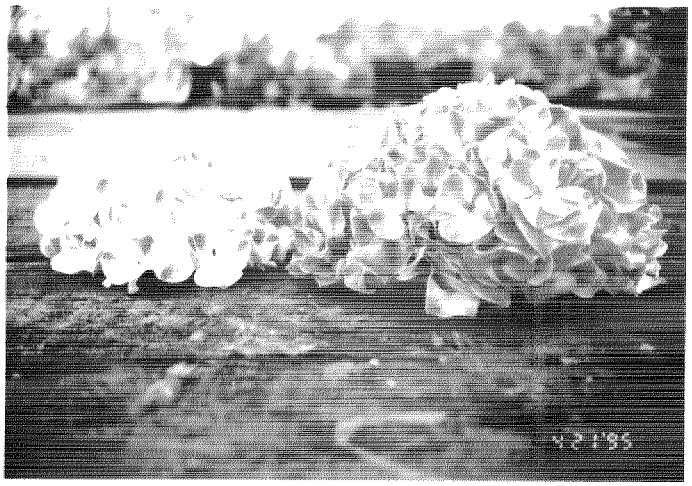
FIG. 7 is a close up view of two blooms: the inflorescence on the left being at the peak of its bloom and the inflorescence on the right being past its peak and close to the stage of fading and developing chlorophyll.
Figure 8:
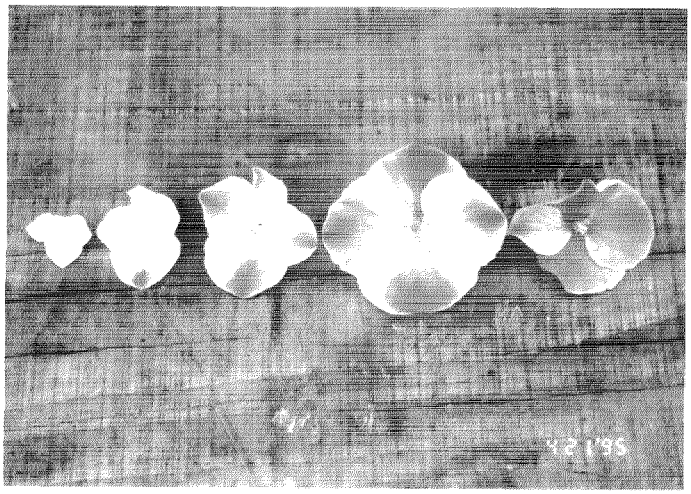
FIG. 8 is a close up view of the sepals in their various stages of growth and bloom, illustrating the development and appearance of the unique pigmentation pattern at its very early stages of formation, at the peak blooming period, and at the mature stage just before fading and developing chlorophyll.
Figure 9:
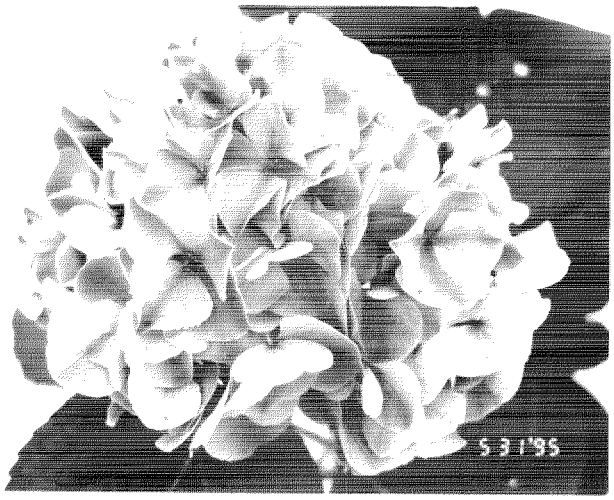
FIG. 9 is a view of one bloom at the stage of developing chlorophyll illustrating how the unique pigmentation pattern still shows as the color fades and the flower dies.

'Ravel' has not been observed under all possible environmental conditions. The phenotype may vary with variations in environment such as temperature, light intensity and day length. The following is a detailed description of the new cultivar as forced under the prevailing daylengths at Half Moon Bay, Calif., under commercial greenhouse conditions at a time appropriate for the sale of the cultivar in the spring. The color determinations were made with The Royal Horticultural Society (R.H.S.) Colour Chart.

The Plant

Origin: Sport of 'Merritts Supreme', a non-patented, commercial Hydrangea.

Classification:

*Botanic.*—*Hydrangea macrophylla* (Thunb.) 'Ravel'.

*Commercial.*—Florist Hydrangea 'Ravel'.

Form: Upright, vigorous compact shrub.

The following table compares the new cultivar with its closest commercial variety of which I am aware.

TABLE OF COMPARISON

| | NEW VARIETY 'RAVEL' | 'MERRITTS SUPREME' |
|---|---|---|
| PLANT: | | |
| HEIGHT | Mean 40 cm, up to 46 cm | mean 34 cm |
| GROWTH | Upright, vigorous; forced easily to bloom in greenhouse; growth regulators necessary to control height | same |
| STEMS | Lateral buds and lenticels are reddish; reddish coloration above and below leaf attachment site | same |
| FOLIAGE | Abundant | same |
| LEAF SIZE | As large as 170 mm long × 152 mm wide | as large as 150 mm long × 140 mm wide |
| SHAPE OF LEAF | Elliptic with acute base and apex; margins are serrate | same |
| TEXTURE OF LEAF | Glabrous; veins dominate on underside and are sunken on surface | same |
| COLOR OF LEAF | Top 137A, underside 137D, veins 145D | Top 139A, underside 137C, veins 145D |
| PETIOLES | to 40 mm length | to 52 mm in length |
| THE BUD: | | |
| FORM | Globose; 4–5 connate petals majority have sepals; those in the very center are non-sepalous | same |
| SIZE | 3 mm | 3 mm |
| PIGMENTATION | green stage - 143D; mature stage - 71C | green stage - 145C; mature stage - 73C |
| POLLEN | white | same |
| BUD ASPECT | Smooth | same |
| RATE OF OPENING | Sepaled buds open slower than non-sepalous buds | same |
| ARRANGEMENT | Borne on 3, 4, or 5 branched panicles | same |
| THE INFLORESCENCE | | |
| TIME OF BLOOMING | Approx. 80 days at 66° F. night temp. | same |
| FORM | Paniculate; 100+ florets per inflorescence both sterile sepalous and fertile non-sepalous on same panicle | same |
| SIZE OF INFLORESCENCE | Size depends on the number of inflorescences per plant | same |
| | Circumference of 5 bloom plant 72.39 cm | Circumference of 5 bloom plant 62.23 cm |
| SHAPE | Spherical clusters of small florets. Sepalous florets are flat and overlap each other. Sepals are persistent. Sepals elongate and mature as the bloom matures. Non-sepalous florets are hidden by sepalous florets | same |
| APPEARANCE | Very Showy | Showy |
| PIGMENTATION OF THE SEPALS | Red-purple group; Sepal tip 67C (seen as dark as 67A); side of tip 68A fading to 68B; white portion is 155A | 66D |
| PERSISTENCE | 4 weeks or more | same |
| FRAGRANCE | Slightly sweet | same |
| FRUIT | none | same |
| REPRODUCTIVE | | |

-continued

TABLE OF COMPARISON

| | NEW VARIETY 'RAVEL' | 'MERRITTS SUPREME' |
|---|---|---|
| ORGANS: | | |
| STAMENS | 7 to 11 (usually 10); pollen is white | 7 to 10 (usually 8) pollen is white |
| STIGMA | One which can be 2 or 3 pronged | same |
| SEPALOUS FLORET: | | |
| NUMBER OF SEPALS | 3 to 5 per floret (usually 4) | same |
| ASPECT OF SEPALS | Smooth | same |
| SHAPE OF SEPALS | Reniform with acuminate apex; edges sometimes serrate | same |
| SIZE OF SEPALS | Usually 1 large, 2 smaller but equally sized, and 1 small sepal | same |
| | Largest measured | Largest measured |

-continued

TABLE OF COMPARISON

| | NEW VARIETY 'RAVEL' | 'MERRITTS SUPREME' |
|---|---|---|
| | 46 mm long × 35 mm wide | 47 mm long × 32 mm wide |
| LARGEST FLORET | 71 mm long × 62 mm wide | 60 mm long × 63 mm wide |
| COLORATION OF SEPALS | See details above Sepal color is determined by soil pH and nutritional amendments supplied | See details above same |

I claim:

1. A new and distinct Hydrangea plant variety of the Saxifragaceae family substantially as herein shown and described.

* * * * *